(12) United States Patent
MacTaggart et al.

(10) Patent No.: US 12,138,186 B2
(45) Date of Patent: Nov. 12, 2024

(54) AUTOMATICALLY DEPLOYABLE INTRAVASCULAR DEVICE SYSTEM

(71) Applicant: Board of Regents of the University of Nebraska, Lincoln, NE (US)

(72) Inventors: Jason N. MacTaggart, Omaha, NE (US); Alexey Kamenskiy, Omaha, NE (US); Blake Marmie, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 976 days.

(21) Appl. No.: 17/258,100

(22) PCT Filed: Jul. 3, 2019

(86) PCT No.: PCT/US2019/040489
§ 371 (c)(1),
(2) Date: Jan. 5, 2021

(87) PCT Pub. No.: WO2020/010194
PCT Pub. Date: Jan. 9, 2020

(65) Prior Publication Data
US 2021/0282950 A1    Sep. 16, 2021

Related U.S. Application Data

(60) Provisional application No. 62/694,054, filed on Jul. 5, 2018.

(51) Int. Cl.
*A61F 2/958*    (2013.01)
*A61B 8/00*    (2006.01)
(Continued)

(52) U.S. Cl.
CPC ............ *A61F 2/958* (2013.01); *A61B 8/0891* (2013.01); *A61B 8/12* (2013.01); *A61B 8/445* (2013.01)

(58) Field of Classification Search
CPC .......... A61F 2/958; A61F 2/95; A61F 2/9517; A61B 8/0891; A61B 8/445
See application file for complete search history.

(56) References Cited

U.S. PATENT DOCUMENTS 5,360,403 A    11/1994    Mische
5,728,068 A *   3/1998    Leone ................ A61M 25/1011
                                                             623/1.11

(Continued)

FOREIGN PATENT DOCUMENTS

WO    WO 1996/038109    12/1996
WO    WO 2000/053240    9/2000

(Continued)

OTHER PUBLICATIONS

European Extended Search Report in European Application No. 16762492.3, dated Feb. 16, 2018, 8 pages.

(Continued)

*Primary Examiner* — Darwin P Erezo
*Assistant Examiner* — Christina C Lauer
(74) *Attorney, Agent, or Firm* — Fish & Richardson P.C.

(57) ABSTRACT

This document describes devices, systems, and methods for automatically deploying intravascular devices. For example, this document describes devices, systems, and methods for automatically deploying and controlling intravascular catheter-based devices for treating catastrophic bleeding from large and medium size vessels such as, but not limited to, the aorta or iliac arteries. In some embodiments, an operator/care giver will simply press the system against the patient's body proximate to a desired site of insertion, or will attach the system to the patient proximate to the desired site of insertion. The operator will then activate the system. Thereafter, the system will use built in imaging (e.g., ultrasound) to locate a proper insertion point and then deploy an access needle to attain vascular access. With that, the system will (Continued)

then automatically insert the intravascular device into the patient.

18 Claims, 6 Drawing Sheets

(51) Int. Cl.
*A61B 8/08* (2006.01)
*A61B 8/12* (2006.01)

(56) References Cited

U.S. PATENT DOCUMENTS

| | | | |
|---|---|---|---|
| 5,868,711 | A | 2/1999 | Kramer et al. |
| 6,148,825 | A * | 11/2000 | Anderson ............ A61M 27/002 604/7 |
| 6,210,318 | B1 * | 4/2001 | Lederman ............ A61M 60/497 600/18 |
| 6,309,350 | B1 | 10/2001 | VanTassel |
| 6,827,735 | B2 | 12/2004 | Greensberg |
| 6,840,956 | B1 | 1/2005 | Wolinsky et al. |
| 10,758,386 | B2 | 9/2020 | MacTaggart et al. |
| 2002/0052648 | A1 * | 5/2002 | McGuckin, Jr. .......... A61F 2/07 623/1.35 |
| 2003/0023299 | A1 | 1/2003 | Amplatz et al. |
| 2003/0229388 | A1 | 12/2003 | Hayashi et al. |
| 2006/0122522 | A1 | 6/2006 | Chavan et al. |
| 2009/0030331 | A1 | 1/2009 | Hochareon |
| 2010/0324649 | A1 | 12/2010 | Mattsson et al. |
| 2012/0191174 | A1 | 7/2012 | Vinluan et al. |
| 2013/0131501 | A1 | 5/2013 | Blaivas et al. |
| 2014/0039537 | A1 | 2/2014 | Carrison |
| 2015/0201910 | A1 | 7/2015 | Zhao et al. |
| 2016/0302772 | A1 * | 10/2016 | Cummins ............ A61B 8/4494 |
| 2016/0317242 | A1 * | 11/2016 | Herlihy .................. A61B 90/11 |
| 2016/0374644 | A1 | 12/2016 | Mauldin, Jr. et al. |
| 2018/0064565 | A1 | 3/2018 | MacTaggart et al. |

FOREIGN PATENT DOCUMENTS

| | | |
|---|---|---|
| WO | WO 2010/029190 | 3/2010 |
| WO | WO 2016/008521 | 1/2016 |
| WO | WO 2016/145163 | 9/2016 |

OTHER PUBLICATIONS

International Preliminary Report on Patentability in Application No. PCT/US2016/021728, dated Sep. 21, 2017, 12 pages.
International Preliminary Report on Patentability in International Appln. No. PCT/US2019/040489, dated Jan. 14, 2021, 9 pages.
International Search Report and Written Opinion in Application No. PCT/US2016/021728, dated Jun. 3, 2016, 13 pages.
International Search Report and Written Opinion in International Appln. No. PCT/US2019/040489, dated Sep. 26, 2019, 10 pages.

* cited by examiner

AUTOMATICALLY DEPLOYABLE INTRAVASCULAR DEVICE SYSTEM

CROSS-REFERENCE TO RELATED APPLICATIONS

This application is a National Stage Application under 35 U.S.C. 8371 and claims the benefit of International Application No. PCT/US2019/040489, filed Jul. 3, 2019, which claims priority to U.S. Patent Application No. 62/694,054 (filed on Jul. 5, 2018), the contents of which is fully incorporated herein by reference.

TECHNICAL FIELD

This document relates to devices, systems, and methods for automatically deploying intravascular devices. For example, this document relates to devices, systems, and methods for automatically deploying and controlling intravascular catheter-based devices for treating catastrophic bleeding from large and medium size vessels such as, but not limited to, the aorta or iliac arteries.

BACKGROUND

Injuries in the United States account for roughly 51% of all deaths among persons 1-44 years of age, which is more than all non-communicable and infectious diseases combined. Exsanguinating non-compressible hemorrhage, mainly from the aorta and its branches, is a major contributor to these mortalities. Causes of such catastrophic bleeding that require the rapid cessation of hemorrhaging vessels include but are not limited to: high-speed motor vehicle accidents, falls from heights, crush injuries, explosions, and gunshot wounds. Many instances of a non-compressible hemorrhage could effectively be controlled with Resuscitative Endovascular Balloon Occlusion of the Aorta (RE-BOA). REBOA often encompasses vascular access through a non-injured artery in the leg or arm, fluoroscopy-guided navigation and deployment of an occlusion balloon proximal to the site of injury. However, complete occlusion of the aorta for prolonged periods of time may result in permanent damage or injury to downstream organs and tissues that are not perfused with blood.

SUMMARY

This document describes devices, systems, and methods for automatically deploying intravascular devices. For example, this document describes devices, systems, and methods for automatically deploying and controlling intravascular catheter-based devices for treating catastrophic bleeding from large and medium size vessels such as, but not limited to, the aorta or iliac arteries. In some embodiments, an operator/care giver will simply press the system against the patient's body proximate to a desired site of insertion, or will attach the system to the patient proximate to the desired site of insertion. The operator will then activate the system. Thereafter, the system will use built in imaging (e.g., ultrasound transducers) to locate a proper insertion point and then deploy an access needle to attain vascular access. With that, the system will then automatically insert the intravascular device into the patient.

Some embodiments of an endovascular device are configured to intravascularly control non-compressible bleeding through a blood vessel while preserving blood flow to organs and tissues that are downstream from the site of the injury. In particular embodiments, the endovascular device includes a stent graft comprising an expandable tubular metallic frame and a covering material disposed on at least a portion of the metallic frame. The stent graft defines a lumen that extends between a first end of the stent graft and a second end of the stent graft. In some embodiments, one or multiple balloons are disposed around an outer periphery of the stent graft. In particular embodiments, two outer periphery balloons are spaced apart from each other. In various embodiments, an additional balloon is disposed within the lumen at a location along the stent graft. This additional balloon can have an inflated configuration that is controllable for fully and/or partially occluding the lumen. In additional embodiments, the stent graft can be integrated with greater and/or fewer balloons along the outer periphery and/or within the lumen to control blood flow within the targeted vessel. In some embodiments, the endovascular device includes one or more sensors in communication with a control system of the deployment system. The sensor(s) and control unit can automate functions of the endovascular device including a diagnosis function and a bleeding reduction function. Accordingly, in some circumstances, endovascular devices provided herein are configured for use in the aorta and/or other blood vessels to endovascularly control the non-compressible bleeding of a patient while preserving and/or controlling the blood flow to organs and tissues that are downstream from the site of injury.

In one aspect, this disclosure is directed to an automated vascular access and endovascular device deployment and control system. In some embodiments, the system includes a housing, a control system coupled to the housing, one or more ultrasound transducers coupled to the housing, a vascular access needle movably coupled to the housing, an endovascular device movably coupled to the needle, and one or more drive systems configured to drive the needle and the endovascular device to extend from the housing and to retract into the housing. The one or more ultrasound transducers are configured for: (i) obtaining image data of subcutaneous structures while the housing is abutted against a skin surface of a patient and (ii) transmitting the image data to the control system.

Such a system may optionally include one or more of the following features. The system may be sized and/or configured to be used in a hand-held manner. The needle may be movable, relative to the housing, between a retracted position in which the needle is within the housing and an extended position in which the needle is outside of the housing or extending away from the housing. The one or more drive systems may include a motor coupled to a pair of rotary guides that are frictionally engaged with the outer surface of the needle so that the rotary guides will move the needle when the rotary guides are rotated by the motor. The one or more drive systems may include a spring that provides motive force to move the needle relative to the housing. The system may also include a spool. In some embodiments, at least a portion of the endovascular device is wound around the spool. In some embodiments, the spool is rotatably driven by the one or more drive systems. The system may also include a compressed gas canister in fluid communication with an inflatable member of the endovascular device. The system may also include a solenoid valve in communication with the control system and arranged to control a flow of gas from the compressed gas canister to the inflatable member. In some embodiments, the endovascular device includes: (i) a stent graft comprising an expandable tubular metallic frame and a covering material disposed on at least a portion of the metallic frame, the stent graft defining a lumen that extends between a first end of the stent graft and a second end of the stent graft: (ii) a first balloon disposed around an outer periphery of the stent graft: (iii) a second balloon disposed around the outer periphery of the stent graft and spaced apart from the first balloon; and (iv) a third balloon disposed within the lumen at a location along the stent graft between the first balloon and the second balloon. The third balloon may have a fully inflated configuration that fully occludes the lumen and a partially inflated configuration that partially occludes the lumen for modulating blood flow through the stent graft. In some embodiments, the control system is configured to control inflation and deflation of each of the first, second, and third balloons individually. The system may also include one or more additional ultrasound transducers coupled to the needle.

In another aspect, this disclosure is directed to a method of automatically deploying an intravascular device in a target blood vessel of a patient. In some embodiments, the method includes: (a) receiving, on a user interface of an automated vascular access and intravascular device deployment and control system ("deployment system"), a user input to activate the deployment system: (b) in response to receiving the input to activate the deployment system, activating, by a control system of the deployment system, one or more ultrasound transducers of the deployment system to generate image data and to transmit the image data to the control system: (c) analyzing, by the control system, the image data to identify the target blood vessel: (d) in response to identifying the target blood vessel, deploying an access needle from the deployment system into the target blood vessel; and (e) deploying the intravascular device over or through the access needle and into the target blood vessel.

Such a method may optionally include one or more of the following features. A machine vision system of the control system may at least partially perform the analyzing of the image data. In some embodiments, the method also includes: during the deploying the access needle, activating by the control system, one or more additional ultrasound transducers coupled to the access needle. In particular embodiments, the method also includes: during the deploying the access needle, steering the access needle based on additional image data generated by the one or more additional ultrasound transducers coupled to the access needle.

In another aspect, this disclosure is directed to a system that includes a housing containing a control system, an ultrasound transducer coupled to the housing, a vascular access needle an endovascular device movably coupled to the housing, and one or more drive systems coupled to the housing and configured to drive the needle and the endovascular device to extend from the housing and to retract into the housing.

Such a system may optionally include one or more of the following features (and/or any of the features listed above). In some embodiments, the ultrasound transducer is configured for: (i) obtaining image data of subcutaneous structures while the housing is abutted against a skin surface of a patient and (ii) transmitting the image data to the control system. The system may be sized to be used in a hand-held manner. The system may also include an additional ultrasound transducer coupled to the needle.

Some or all of the embodiments described herein may provide one or more of the following advantages. First, some systems described herein can provide automated vascular access and deployment of an intravascular device such as, but not limited to, a REBOA balloon catheter or a REBOA endovascular stent graft device. Using such systems, reliable and rapid precision needle placement can be attained to improve patient outcomes, reduce procedure times, and reduce complications and long-term costs.

Second, the systems described herein are configured to operate automatically or semi-automatically. In some embodiments, an operator/care giver will simply press the system against the patient's body proximate to a desired site of insertion, or will attach the system to the patient proximate to the desired site of insertion. The operator will then activate the system. Thereafter, the system will use built in imaging (e.g., ultrasound) to locate a proper insertion point and then deploy an access needle to attain vascular access. Thereafter, the system will automatically insert the intravascular device into the patient. Consequently, with such a high level of automation, little skill or training is required by the operator to use the systems. Moreover, in some embodiments the system can provide visual and/or audible instructions to an operator to help the operator use the system properly.

Third, in some cases catastrophic bleeding can be controlled using the devices, systems, and methods provided herein. Moreover, some embodiments can be advantageously used to detect and precisely isolate the location of bleeding. For example, some embodiments can serve both as an endovascular intracorporeal-vascular shunt to redirect or distribute blood flow as well as a complete occlusion device to aid in the localization and rapid cessation of a non-compressible hemorrhage.

Fourth, in some optional embodiments, a computerized control unit of the system can deploy the stent graft and balloons in response to hemodynamic parameters detected by one or more sensors coupled to the stent graft. In that manner, the stent graft and balloons can selectively isolate segments of the vessel to stop or slow hemorrhage, and can do so while reducing the potential for human errors. In addition, in some embodiments the one or more sensors can sense pressure and/or blood flow difference(s) within the vasculature to determine the location of bleeding and, in response, the control unit can inflate and/or deflate balloons to re-establish blood flow to unaffected areas. In doing so, the system reduces blood loss through the injured vessel while maintaining its integrity to nourish the downstream organs and tissues. Hence, better patient outcomes can be achieved.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
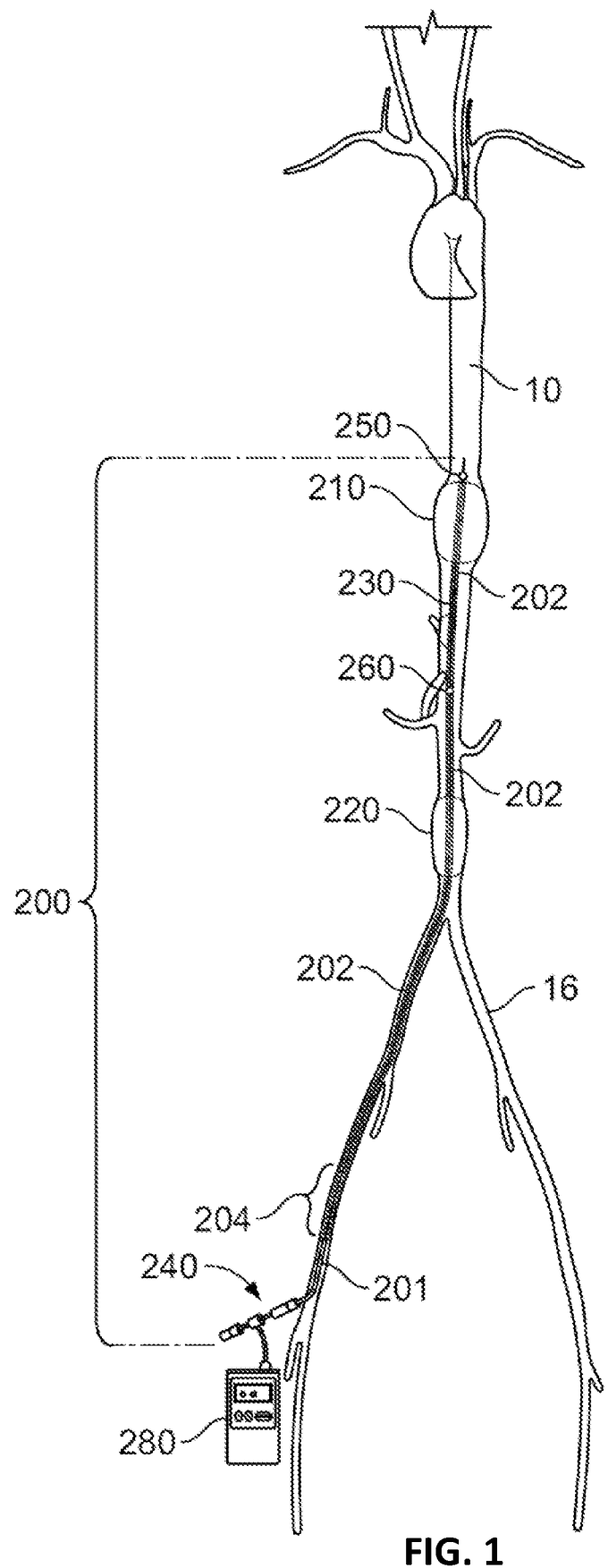
FIG. 1 is an illustration of a portion of a human vasculature, including an aorta and its branches, containing an example endovascular device with one internal and two external balloons coupled to a control unit in accordance with some embodiments.

Referring to FIG. 1, an example REBOA endovascular stent graft device 200 can be deployed in a blood vessel 10 (e.g., aorta). As described herein, the REBOA endovascular stent graft device 200 can be operated in a manner that reduces blood loss through an injured vessel while allowing blood flow to downstream organs and tissues. This is also described in international application PCT/US2016/021728 (published as WO2016/145163), which is expressly incorporated herein by reference in its entirety and for all purposes.

The REBOA endovascular stent graft device 200 includes a catheter 201, a stent graft 202, a first balloon 210, a second balloon 220, a third balloon 230, a catheter hub 240, a first sensor 250, and a second sensor 260. In some embodiments, a control unit 280 is coupleable to the REBOA endovascular stent graft device 200 to comprise a system for controlling catastrophic bleeding from blood vessels.

The stent graft 202 defines a lumen that extends between the ends of the stent graft 202 (between the proximal and distal ends which are open). The catheter 201 is coupled to the catheter hub 240 and to the stent graft 202. The first balloon 210 and the second balloon 220 are coupled around an outer periphery of the stent graft 202. As such, the first balloon 210 and the second balloon 220 do not occlude the lumen of the stent graft 202. The third balloon 230 is disposed within the lumen of the stent graft 202. Therefore, when the third balloon 230 is inflated, the third balloon 230 can occlude the lumen of the stent graft 202 (e.g., like the balloon 130 of stent graft device 100 described above in reference to FIGS. 1-3). Depending on the extent of inflation (as controlled by the clinician or control unit 280), the third balloon 230 can either partially or fully occlude the lumen of stent graft 202. The catheter hub 240 is coupleable to the control unit 280.

In some embodiments, the REBOA endovascular stent graft device 200 can be passed into the patient's vasculature via a percutaneous access site such as, but not limited to, a femoral artery, a radial artery, a subclavian artery, brachial artery, and the like. The approach can be retrograde or antegrade. In some embodiments, the REBOA endovascular stent graft device 200 (and/or a guidewire) can be navigated within the vasculature using one or more imaging modalities such as, but not limited to, x-ray fluoroscopy, ultrasound, MRI, and the like. In some embodiments, a guidewire may be placed within the vasculature first and the REBOA endovascular stent graft device 200 can be deployed over the guidewire.

The REBOA endovascular stent graft device 200 is retrievable from the patient's vasculature. For example, in some embodiments the REBOA endovascular stent graft device 200 can be recaptured into a sheath and then the sheath containing the device 200 can be removed from the patient's vasculature. Hence, the REBOA endovascular stent graft device 200 is configured to be temporarily implanted.

The catheter 201 is an elongate flexible member that defines at least one lumen (for carrying inflation media). The catheter 201 can comprise a tubular polymeric or metallic material. For example, in some embodiments the catheter 201 can be made from polymeric materials such as, but not limited to, polytetrafluoroethylene (PTFE), fluorinated ethylene propylene (FEP), HYTREL®, nylon, PICOFLEX®, PEBAX®, TECOFLEX®, and the like, and combinations thereof. In alternative embodiments, the catheter 201, or portions thereof, can be made from metallic materials such as, but not limited to, nitinol, stainless steel, stainless steel alloys, titanium, titanium alloys, and the like, and combinations thereof. In some embodiments, the catheter 201 can be made from combinations of such polymeric and metallic materials (e.g., polymer layers with metal braid, coil reinforcement, stiffening members, and the like, and combinations thereof). In particular embodiments, some longitudinal portions of the catheter 201 may be configured to have different mechanical properties than other longitudinal portions of the catheter 201. For example, some portions may be stiffer, more lubricious, have greater column strength, may be more flexible, may have a smaller or larger diameter, and the like, as compared to other portions of the catheter 201. In some embodiments, one or more radiopaque markers can be located on the catheter 201. In the case of a braided stent catheter 201, the braid angle and/or other construction parameters can be selected to resist balloon force to keep the catheter 201 from collapsing from the balloon force.

The stent graft 202 is made of one or more elongate members. In some embodiments, the elongate members of the stent graft 202, are formed from a single piece of precursor material (e.g., sheet or tube) that is cut, expanded, and then shape-set in the expanded configuration. For example, some embodiments are fabricated from a tube that is laser-cut (or machined, chemically etched, water-jet cut, etc.) and then expanded and heat-set into its final expanded size and shape. In some embodiments, the stent graft 202 is created compositely from multiple elongate members (e.g., wires or cut members) that are joined together to form the stent graft 202. In some embodiments, the stent graft 202 is made of one or more wires that is/are braided or woven to form a mesh-like structure.

The elongate members of the stent graft 202 can be comprised of various materials and combinations of materials. In some embodiments, nitinol (NiTi) is used as the material of the elongate members of the stent graft 202, but other materials such as stainless steel, L605 steel, polymers, MP35N steel, stainless steels, titanium, cobalt/chromium alloy, polymeric materials, Pyhnox, Elgiloy, or any other appropriate biocompatible material, and combinations thereof can be used. The super-elastic properties of NiTi make it a particularly good candidate material for the elongate members of the stent graft 202 because, for example, NiTi can be heat-set into a desired shape. That is, NiTi can be heat-set so that the stent graft 202 tends to self-expand into a desired shape when the stent graft 202 is unconstrained. In some embodiments, the stent graft 202 is comprised of NiTi, for example, so it may have a spring nature that allows the stent graft 202 to be elastically collapsed or "crushed" to a low-profile delivery configuration, and then to reconfigure to the expanded configuration as shown in FIG. 1. The stent graft 202 may be conformable, fatigue resistant, and elastic such that the stent graft 202 can conform to the topography of the surrounding vasculature when the stent graft 202 is deployed in a vessel of a patient.

In some embodiments, the stent graft 202 includes one or more eyelets or other types of attachment features. In particular embodiments, the stent graft 202 includes a lasso-like member threaded through multiple portions of the stent graft 202 such that the stent graft 202 can be cinched to a smaller diameter by tensioning the lasso member to assist in retrieval of the stent graft 202. One or more radiopaque markers may be included on some embodiments of the stent graft 202.

In some embodiments, the stent graft 202 includes a covering material on at least a portion of the stent graft 202, or on the entire stent graft 202. It should be understood, that such a covering material is optional, in some embodiments. That is, in some embodiments the stent is a bare stent. The covering material may provide enhanced sealing between the stent graft 202 and the vessel wall in some cases. In some embodiments, two or more portions of covering material, which can be separated and/or distinct from each other, can be disposed on the stent graft 202. That is, in some embodiments a particular type of covering material is disposed on some areas of the stent graft 202 and a different type of covering material is disposed on other areas of the stent graft 202.

In some embodiments, the covering material, or portions thereof, comprises a hydrophobic fluoropolymer, such as an expanded polytetrafluoroethylene (ePTFE) polymer. In some embodiments, the covering material, or portions thereof, comprises a polyester, a silicone, a urethane, ELAST-EON™ (a silicone and urethane polymer), another biocompatible polymer, DACRON®, polyethylene terephthalate (PET), copolymers, or combinations and subcombinations thereof. In some embodiments, the covering material is manufactured using techniques such as, but not limited to, electrospinning, extrusion, expansion, heat-treating, sintering, knitting, braiding, weaving, chemically treating, and the like. In some embodiments, the covering material, or portions thereof, comprises a biological tissue. For example, in some embodiments the covering material can include natural tissues such as, but not limited to, bovine, porcine, ovine, or equine pericardium. In some such embodiments, the tissues are chemically treated using glutaraldehyde, formaldehyde, or triglycidylamine (TGA) solutions, or other suitable tissue crosslinking agents.

In some embodiments, the covering material is disposed on the interior and the exterior of the framework of the stent graft 202. In some embodiments, the covering material is disposed on the just the exterior of the framework of the stent graft 202. In some embodiments, the covering material is disposed on the just the interior of the framework of the stent graft 202. In some embodiments, some portions of the framework of the stent graft 202 are covered by the covering material in a different manner than other portions of the framework of the stent graft 202.

The REBOA endovascular stent graft device 200 is expandable between a low-profile configuration and a diametrically expanded, deployed configuration. FIG. 1 shows the REBOA endovascular stent graft device 200 in the diametrically expanded, deployed configuration. In the deployed configuration, some portions of the stent graft 202 may make full peripheral contact with the inner wall surface of the vessel 10, while some other portions may not make full peripheral contact with the inner wall surface of the vessel 10. In some embodiments, the REBOA endovascular stent graft device 200 can be deployed into the vasculature (e.g., blood vessel 10) using a delivery sheath.

A distal portion of the delivery sheath containing the REBOA endovascular stent graft device 200 can be passed into the patient's vasculature via a percutaneous access site such as, but not limited to, a femoral artery (as shown in FIG. 1), femoral vein, a radial artery, a brachial artery, a subclavian artery, and the like. The approach can be retrograde or antegrade. In some embodiments, the delivery sheath can be navigated within the vasculature using one or more imaging modalities such as, but not limited to, x-ray fluoroscopy, ultrasound, intravascular ultrasound (IVUS), and the like. In some embodiments, a guidewire may be placed within the vasculature first and the delivery sheath can be deployed over the guidewire.

While the REBOA endovascular stent graft device 200 is depicted as being deployed within an aorta (blood vessel 10), it should be understood that other vessels may be treated using the REBOA endovascular stent graft device 200. That is, the REBOA endovascular stent graft device 200 is scalable to smaller sizes for use in other areas of a patient's vasculature. Moreover, the REBOA endovascular stent graft device 200 can be used to treat venous bleeding (such as retrohepatic vena cava injuries), pelvic hemorrhages or fractures, and uterine or gastrointestinal bleeding, to provide a few examples.

When the REBOA endovascular stent graft device 200 (within the delivery sheath) is positioned at a target location in the vasculature, the delivery sheath can be pulled back while the position of the catheter 201 is maintained substantially stationary. Alternatively, or additionally, the catheter 201 can be advanced distally in relation to the delivery sheath. Such relative motions of the catheter 201 and the delivery sheath can cause the REBOA endovascular stent graft device 200 to be expressed from the delivery sheath at the target site.

In some embodiments, the stent graft 202 will self-expand to the deployed configuration. Alternatively, or additionally, in some embodiments, one or more balloons can be used to expand some or all of the stent graft 202. While the stent graft 202 is deployed and in the expanded configuration inside of the blood vessel 10, in some cases the REBOA endovascular stent graft device 200 is temporarily anchored in relation to the blood vessel 10.

The REBOA endovascular stent graft device 200 is retrievable from the patient's vasculature. That is, the REBOA endovascular stent graft device 200 can be recaptured into a sheath and then the sheath containing the stent graft device 200 can be removed from the patient's vasculature. Hence, the REBOA endovascular stent graft device 200 is configured to be temporarily implanted.

In some embodiments, the catheter 201 includes multiple lumens through which inflation media (e.g., liquid or gas) can be passed, to individually and independently inflate and deflate the balloons 210, 220, and 230 (and any additional balloons that are included in some embodiments but not depicted herein). The catheter 210 can be made of any of the materials described above in reference to catheter 110. In some embodiments, rather than using a single multi-lumen catheter 201, two or more separate catheters may be included with lumens for supplying inflation media to the balloons 210, 220, and/or 230 (and other balloons if so configured).

In some embodiments, the stent graft 202 is an elongate stent graft comprising an expandable tubular metallic frame and a covering material disposed on at least a portion of the metallic frame. The stent graft 202 (e.g., the elongate members and covering material) can be made of any of the materials described above in reference to stent 120.

The first and second balloons 210 and 220 are disposed around the outer periphery of the stent graft 202. The first and second balloons 210 and 220 are spaced apart from each other (with the third balloon 230 disposed between the first and second balloons 210 and 220). The first and second balloons 210 and 220 can be inflated such that the outer peripheries of the first and second balloons 210 and 220 make full peripheral contact with the inner wall surface of the vessel 10. Hence, while the first and second balloons 210 and 220 are inflated, a seal between the first and second balloons 210 and 220 and the vessel 10 is created. Therefore, blood flowing through the vessel 10 will be directed (shunted) into the lumen of the stent graft 202 while the first and second balloons 210 and 220 are inflated and in full peripheral contact with the inner wall surface of the vessel 10.

The third balloon 230 is disposed within the lumen of the stent graft 202. The third balloon 230 can be inflated to fully occlude the interior of the stent graft 202. In such a case, essentially no blood will be allowed to flow through the lumen of the stent graft 202. In addition, the third balloon 230 can be partially inflated to partially occlude the interior lumen of the stent graft 202. Hence, the extent of inflation of the third balloon can be selectively controlled to modulate the blood flow through the lumen of the stent graft 202. The third balloon 230 can also be deflated to a very small size such that it only minimally impedes blood flow through the lumen of the stent graft 202.

The balloons 210, 220, and 230 (and/or any additional balloons included but not depicted in the figures) can be made of any suitable materials such as silicone. Other materials such as, but not limited to, latex, fluoroelastomers, polyurethane, polyethylene terephthalate (PET), and the like, are used in some embodiments.

Again, the third balloon 230 can be selectively inflated to a partially inflated configuration such that the third balloon 230 partially occludes the interior of the stent graft 202. That is, the size of the third balloon 230 can be adjusted by a clinician, or by the automated control unit 280, by selectively filling the third balloon 230 with an amount of inflation media (e.g., saline, CO2, etc.) that only partially fills the capacity of the third balloon 230. In that manner, the extent of occlusion of the lumen of the stent graft 202 by the partially inflated third balloon 230 can be selected/controlled, and therefore the amount of blood flow through the lumen of the stent graft 202 can be modulated.

Figure 2:
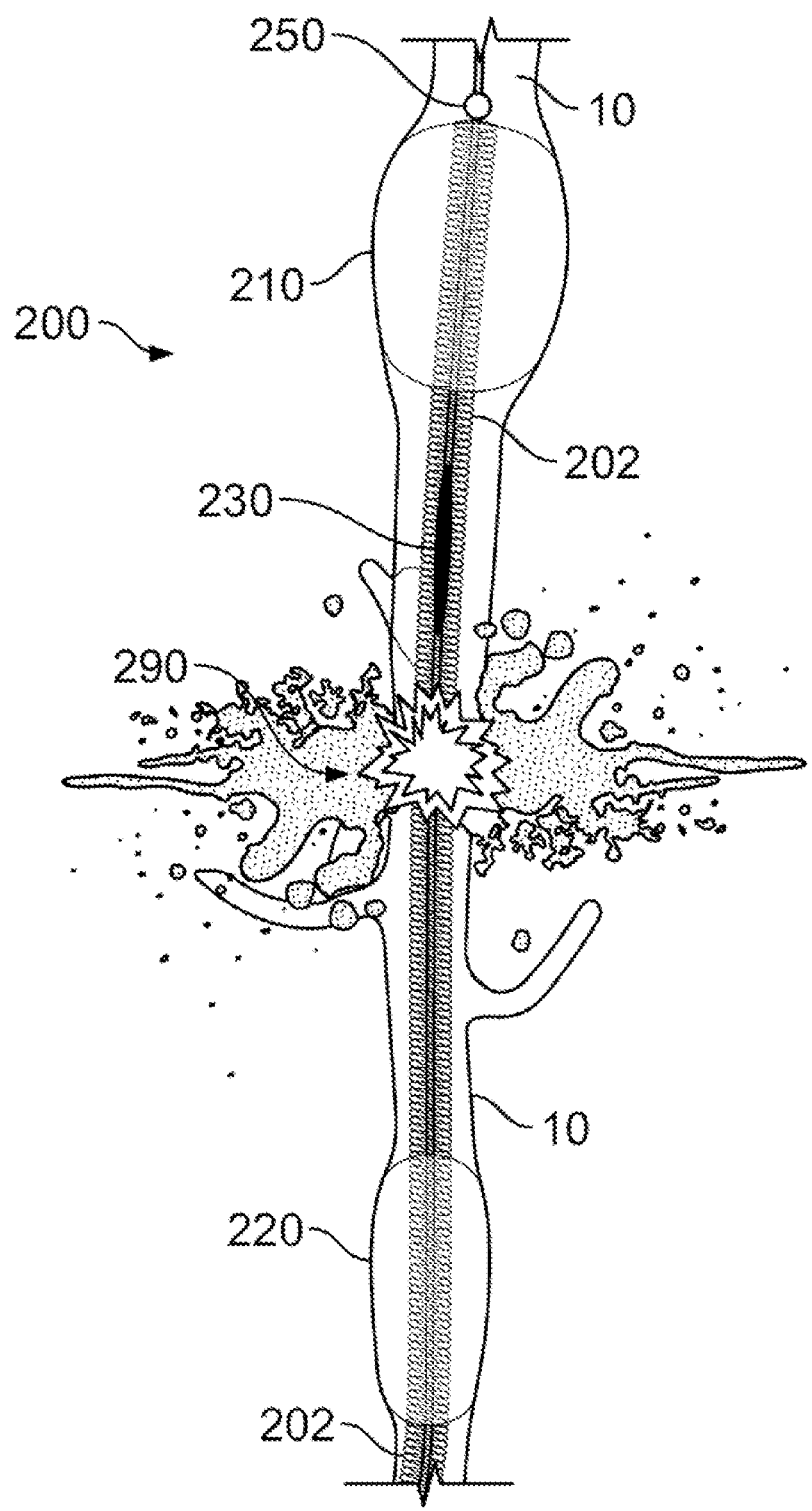
FIG. 2 is an illustration of a portion of a human vasculature, including a hemorrhage site, being treated using the endovascular device of FIG. 1.
Figure 3:
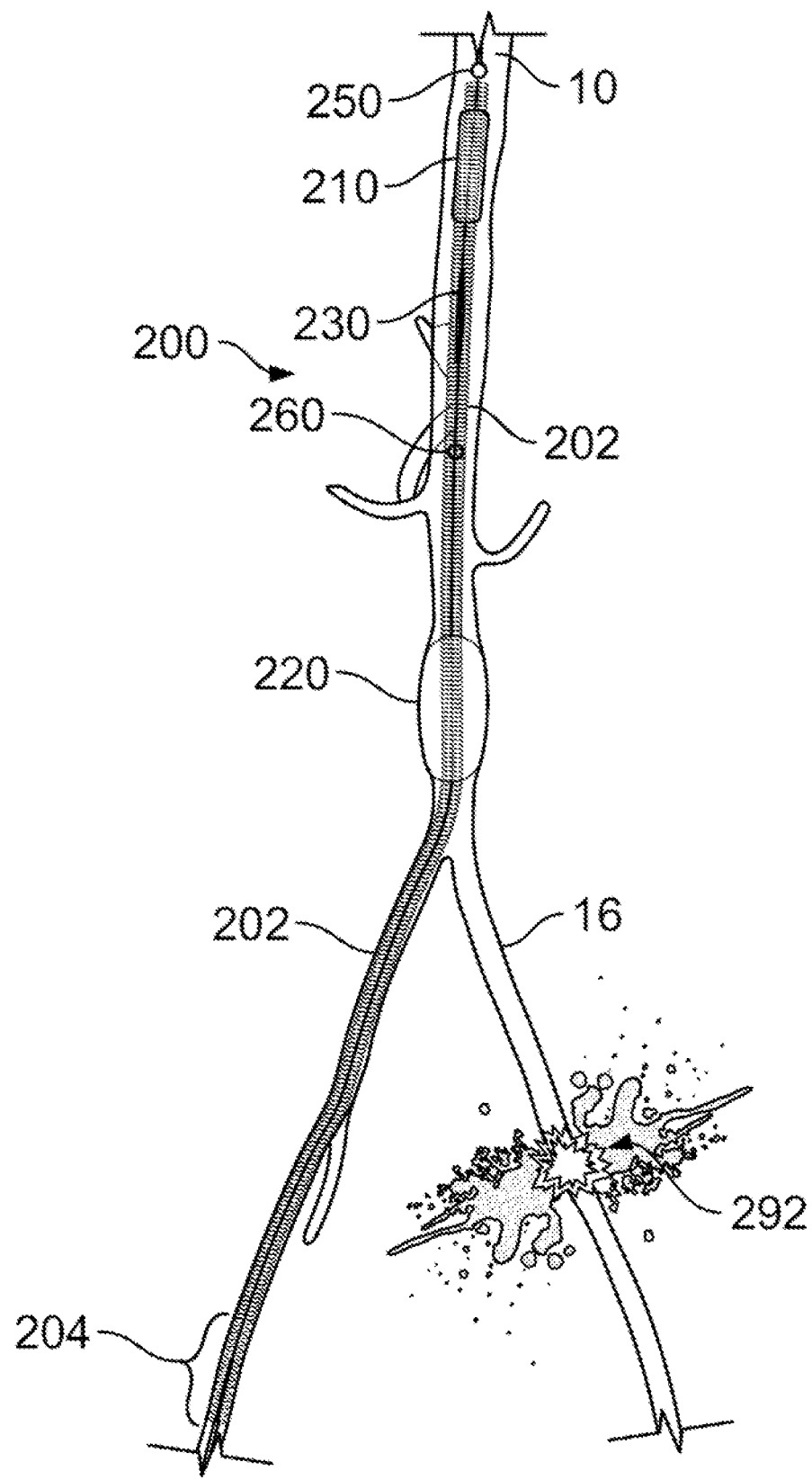
FIG. 3 is another illustration of a portion of a human vasculature, including a hemorrhage site, being treated using the endovascular device of FIG. 1.

Referring also to FIGS. 2 and 3, in some implementations, the REBOA endovascular stent graft device 200 is configured to serve as an endovascular-vascular shunt to aid in rapid cessation of various types of non-compressible hemorrhages associated with the aorta or other vessels. Alternative configurations of the REBOA endovascular stent graft device 200 can be implemented to provide occlusions of vessels dependent on the site of injury. In some embodiments, such alternative configurations can be automatically made by the control unit 280 in conjunction with the REBOA endovascular stent graft device 200.

For visceral injuries (as shown in FIG. 2), the first and second balloons 210 and 220 are inflated to prevent blood flow to the injury 290, while the third balloon 230 remains deflated, which allows blood perfusion of the lower extremities and pelvis by shunting blood through the stent graft 202.

In the event of a pelvic injury (as depicted by FIG. 3), the REBOA endovascular stent graft device 200 can be deployed and configured to allow blood flow to upstream branch vessels and the adjacent branching pelvic vessel while mitigating hemorrhage from the injury 292 in the branching leg vessel 16. In a first example, pertaining to the depicted embodiment that includes a fully covered stent graft 202 between the second balloon 220 and the uncovered portion 204, both the first balloon 210 and the third balloon 230 can be deflated (while the second balloon 220 is inflated). In result, blood will be allowed to flow between the exterior surface of the first balloon and the inner wall of the vessel 10. Such blood flow will thereby nourish branch vessels (such as the renal arteries, etc.). In addition, blood will flow within the lumen of the stent graft 202 to nourish the adjacent branching pelvic vessel. However, blood flow to the injury 292 in the branching leg vessel 16 will be substantially cut off. In a second example, pertaining to embodiments that have uncovered or open areas in the stent graft 202 proximally adjacent to the second balloon 220, the first balloon 210 can be deflated and the third balloon 230 can be inflated (while the second balloon 220 is inflated). By deflating the first balloon 210, blood flow will thereby be allowed to nourish branch vessels (such as the renal arteries, etc.) that are upstream of second balloon 220. By inflating third balloon 230, blood will be prevented from flowing through the lumen of the stent graft 202 and exiting through open or uncovered areas of the stent graft 202 to flow into the branching leg vessel 16. Hence, blood flow to the injury 292 will be substantially cut off.

In some embodiments, sensors 250 and 260 embedded in or coupled to the stent graft 202 can determine the location of the injury (e.g., injury 290, injury 292, and the like) by detecting hemodynamic changes within the patient's vasculature to determine and automatically (or semi-automatically) control the selective function of the separate balloons 210, 220, and 230.

Figure 4:
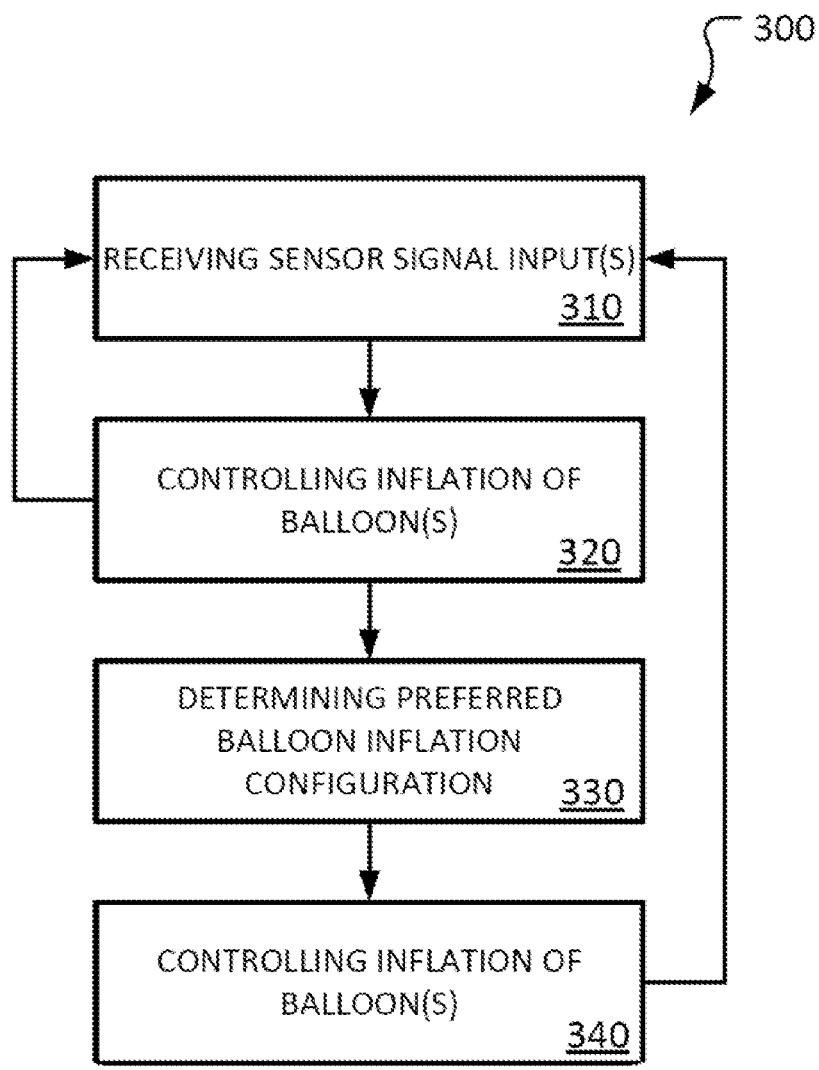
FIG. 4 is a flowchart of an example method of controlling the endovascular device of FIG. 1 using a computerized control unit.

FIG. 4 provides a flowchart of an example method 300 for controlling the endovascular device 200 of FIGS. 1-3 by a computerized control unit (e.g., control unit 280). The method 300 is performed while the REBOA endovascular stent graft device 200 is within the vasculature of the patient and the computerized control unit is coupled with the REBOA endovascular stent graft device 200.

It should be understood that automating the control of the REBOA endovascular stent graft device 200 can be particularly advantageous in the emergency care setting. That is the case because emergency situations can be quite chaotic, and humans may have difficulties properly diagnosing and treating hemorrhage conditions is such situations. Hence, by automating or semi-automating the use of the REBOA endovascular stent graft device 200, better patient outcomes may be realized in some cases.

At step 310, the computerized control unit receives input signals from one or more sensors of the REBOA endovascular stent graft device 200. For example, at step 310 the computerized control unit can receive signals that are indicative of blood pressure and/or blood flow rates from one or more sensors such as the sensors 250 and/or 260 of the REBOA endovascular stent graft device 200. Such one or more sensors can additionally or alternatively be located at one or more other locations along the REBOA endovascular stent graft device 200. In addition, as described above, signals that are indicative of various other relevant parameters (blood gases (e.g., O2, CO2, etc.), temperature, pH, heart rate, etc.) can be received by the computerized control unit.

At step 320, the computerized control unit controls the inflation and deflation of the balloons of the endovascular device. For example, using the REBOA endovascular stent graft device 200 to illustrate this step, in some cases the computerized control unit may inflate first balloon 210, inflate third balloon 230, and deflate second balloon 220. After doing so, the method 300 can revert to step 310 and the computerized control unit can receive a second round of input signals from the one or more sensors 250 and 260 of the REBOA endovascular stent graft device 200. The control unit, knowing which balloons are inflated and deflated, can use the second round of input signals from the one or more sensors 250 and 260 in step 330 described below. After receiving the second round of input signals, the control unit may control the inflation of the balloons again (e.g., in another configuration) per step 320. Thereafter, the control unit can once again receive another round of input signals (per step 310) from the one or more sensors 250 and 260 of the REBOA endovascular stent graft device 200. The steps 320 and 310 can be repeated for multiple cycles. In some cases, for each time step 320 is performed, the particular configuration of balloon inflation/deflation can be different. By performing these repetitive steps, in some cases the control unit can obtain the data it needs to diagnose the location of a hemorrhage.

At step 330, the computerized control unit uses the data from the repetitive performance of steps 310 and 320 (as described above) to determine a preferred balloon inflation and/or deflation configuration. For example, using the REBOA endovascular stent graft device 200 to illustrate this step, the data from the repetitive performance of steps 310 and 320 may indicate that a hemorrhage may be located between the first and second balloons 210 and 220 (as exemplified in FIG. 5). Using such information, the computerized control unit may determine that the preferred balloon inflation and/or deflation configuration is to inflate first balloon 210, inflate second balloon 220, and deflate balloon 230. It should be understood that this is merely one non-limiting example of how the computerized control unit can perform step 330.

At step 340, after determining the preferred balloon inflation and/or deflation configuration in step 330, the control unit controls the inflation and/or deflation of the balloon(s) to implement the preferred balloon inflation and/or deflation configuration. For example, the control unit may inflate first balloon 210, inflate second balloon 220, and deflate balloon 230 (e.g., per FIG. 2). In another example, the control unit may deflate first balloon 210, inflate second balloon 220, and deflate third balloon 230 (e.g., per FIG. 3). It should be understood that multiple other variations of the preferred balloon inflation and/or deflation configuration that can be implemented in step 340 are also envisioned within the scope of this disclosure.

Figure 5:
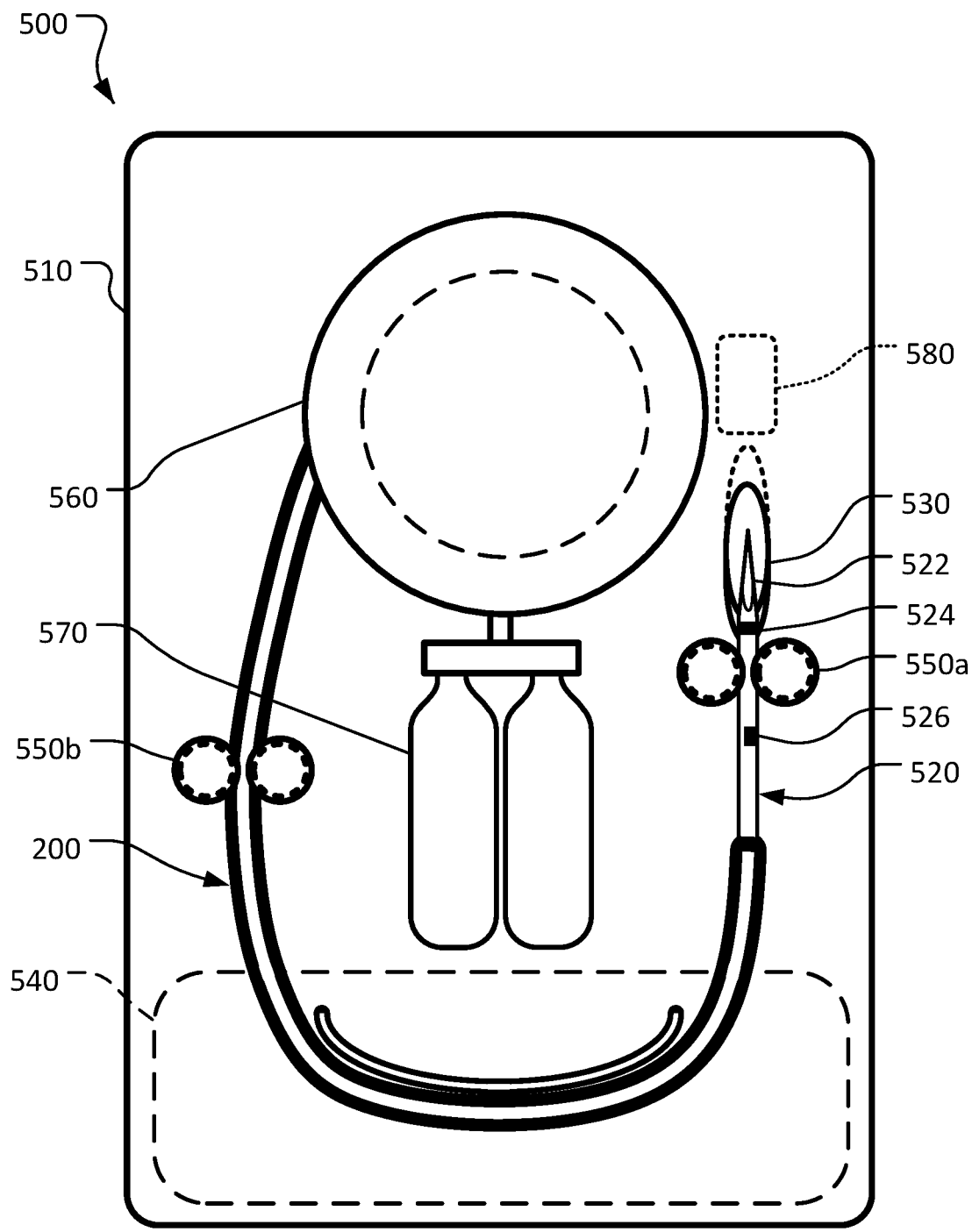
FIG. 5 is a top view of the internal components of an example automated vascular access and endovascular device deployment/control system in accordance with some embodiments.
Figure 6:
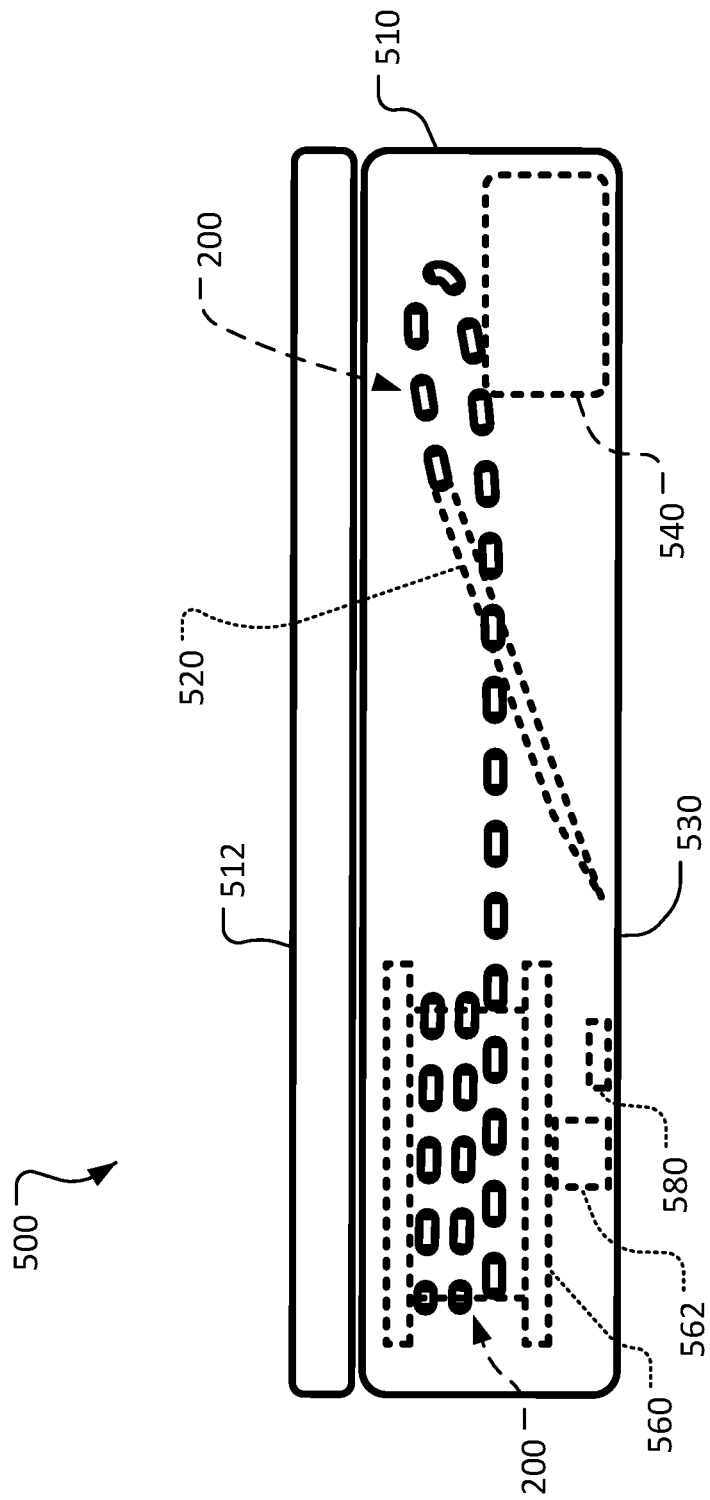
FIG. 6 is a side view of the automated vascular access and endovascular device deployment/control system of FIG. 5.

FIGS. 5 and 6 illustrate an example automated vascular access and endovascular device deployment/control system 500 (or simply the "system 500") in accordance with some embodiments. In some embodiments, the system 500 can deploy an intravascular device such as, but not limited to, the REBOA balloon catheter, or a REBOA endovascular stent graft device 200. The deployment of the intravascular device can take place in an automated or semi-automated manner using the system 500, as described further below:

The system 500 is a hand-held device that can be used by a person with minimal training. The system 500 is particularly well-suited for use outside the hospital environment, such as in conjunction with ambulances, military bases, battle fields, and other contexts in which intravascular devices may need to be deployed in an emergency situation outside of a hospital. However, the system 500 is also well-suited for use in the hospital environment, including in emergency rooms, surgery and other hospital contexts.

Again, the system 500 can be used to deploy and operate the REBOA endovascular stent graft device 200. The system 500 can also be used to deploy and operate other types of REBOA devices such as, but not limited to, the ER-REBOA™ catheter sold by PRYTIME MEDICAL™, and other iterations/variations of REBOA-type devices. Moreover, the system 500 can be adapted to deploy other types of intravascular devices such as, but not limited to an ECMO catheter, perfusion devices, PICC line, and the like. Additionally, the system 500 is well-suited to be used in conjunction with robotic surgery or tele-operated surgery systems.

In the depicted embodiment, the automated vascular access and endovascular device deployment/control system 500 includes a housing 510, user interface 512, access needle 520, needle deployment opening 530, control system 540, guides 550a and 550b, spool 560, compressed gas canister(s) 570, and one or more ultrasound transducer(s) 580.

The housing 510 is designed to be hand-held. In some embodiments, straps for attaching the system 500 to a limb (e.g., thigh, arm, neck, etc.) of a patient are attached to and extend from the housing 510. In some embodiments, one or more adhesive patches is/are included on the bottom face of the housing 510 to facilitate attachment to a skin surface of a patient. The housing 510 defines the needle deployment opening 530 through the bottom of the housing 510 so that the access needle 520 can extend from the housing 510 through the needle deployment opening 530.

The user interface 512 (which is not shown in FIG. 5 so that the internal components of the system 500 are more clearly visible) is coupled to the housing 510. In some embodiments, the user interface 512 is movably coupled to the housing 510 (such as hinged together like a book), so that the user interface 512 can be moved in relation to the housing to open up the system 500 (e.g., to access the internal components as illustrated in FIG. 5). The user interface 512 can include components such as, but not limited to, a display (including a touchscreen type of display), buttons, a speaker for audio output, microphone for audio input, indicator lights, and so on, in accordance with state of the art user interfaces.

The system 500 also includes the control system 540. The control system 540 as used herein broadly encompasses various types of components such as, but not limited to, an energy source (e.g., one or more onboard batteries), computer-readable memory (e.g., storing algorithms and executable instructions, and storing data accessed by the system 500 during use, and the like), one or more processing units (e.g., chips and/or chip sets that include separate and multiple analog and/or digital processors) for controlling the system 500 during use, a machine vision system, communications interface(s) (e.g., wireless interface for communications with external devices/systems), sensor/device interfaces (e.g., for interfacing with ultrasound transducers, the user interface, camera, and the like), motor drive/control systems, and so on, in accordance with state of the art control systems.

The system 500 also includes the access needle 520. The access needle 520 is driven by the system 500 into and/or along a vessel of a patient to deploy an intravascular device (e.g., the REBOA endovascular stent graft device 200 in this example). In some embodiments, the access needle 520 is propelled through needle deployment opening 530 at an angle between 15° and 45° relative to the bottom surface of the housing 510. The access needle 520 includes a beveled tip. The bevel can be oriented up or down relative to the bottom surface of the housing 510. The access needle 520 can be hollow or have a solid core.

In some embodiments, the access needle 520 is deployed from the housing 510 such that it punctures the skin of the patient to attain vascular access. In some such cases, the user can manually apply force to compress the system 500 against the skin surface of the patient to provide back-pressure so that the access needle 520 successfully punctures the skin and tissues of the patient to attain vascular access.

Alternatively, in some embodiments a skin incision ("nick") is made manually by a user (e.g., using a scalpel or other type of knife), and the access needle 520 is thereafter deployed from the housing 510 such that it is advanced through the incision to attain vascular access. For example, a skin incision (about 1 cm in length) can be manually made and then the system 500 can be positioned over the incision so that the access needle 520 will egress from the housing 510 and pass through the incision. In some embodiments, the housing 510 has a projection around the needle deployment opening 530 that can be placed into or around the manually-made incision to facilitate proper alignment of the access needle 520 to the incision.

In some embodiments, the system 500 includes a blade that is manually deployable or automatically deployed to create a skin incision. The access needle 520 is thereafter deployed from the housing 510 such that it is advanced through the incision to attain vascular access.

The system 500 also includes the one or more ultrasound transducer(s) 580. The one or more ultrasound transducer(s) 580 are used, for example, to automate the identification of an access vessel so that the access needle 520 can be deployed in a desired location to attain entry into the access vessel. This manner of operation can make a lower skilled individual successful at precision needle placement. Accordingly, reliable and rapid precision needle placement can improve patient outcomes, reduce procedure times, and reduce complications and long-term costs.

To begin operation of the system 500, a user can place the system 500 against a body part (e.g., leg, arm, neck, torso, etc.) of a patient and then activate the system 500 so that the one or more ultrasound transducer(s) 580 begin scanning and sending data to the control system 540. The control system 540 can use its algorithms and machine vision system capabilities to identify structures below the skin surface of the patient in search of a desired access vessel (e.g., femoral artery, radial artery, subclavian artery, brachial artery, and the like). The control system 540, using the data from the one or more ultrasound transducer(s) 580, can determine factors such as, but not limited to, blood flow direction, flow rates, vessel sizes, vessel shapes, etc.

If the control system 540 identifies a desired access vessel and determines that the system 500 is suitably positioned relative to the patient such that the access needle 520 can be driven to enter the desired access vessel upon deployment, then the control system 540 can use the user interface 512 to provide instructions to the user to continue to hold the system 500 in the current position and to initiate deployment of the access needle 520. If the control system 540 identifies a desired access vessel and determines that the system 500 is not suitably positioned relative to the patient such that the access needle 520 will enter the desired access vessel upon deployment, then the control system 540 can use the user interface 512 to provide instructions to the user to move the housing 510 in a particular manner so that the system 500 becomes suitably positioned.

If the control system 540, using the data from the one or more ultrasound transducer(s) 580, is unable to identify a desired access vessel, then the control system 540 can use the user interface 512 to provide instructions to the user to move the housing 510 to a different location on the patient (e.g., "move the housing 2 inches higher on the leg," or "move the housing 1 inch towards the patient's midline"). The instructions provided can include general terms and/or images to, for example, position the system 500 on an upper thigh or groin of the patient.

If the control system 540, using the data from the one or more ultrasound transducer(s) 580, is able to identify two or more vessels but is unable to determine which of the two or more vessels is the desired vessel (e.g., the femoral artery (desired for aortic access) versus the femoral vein (not desired for aortic access)), then the control system 540 can use the user interface 512 to provide instructions to prompt the user to perform actions that may help the control system 540 to distinguish between the two or more vessels to identify the desired vessel. For example, an instruction to temporarily compress the patient's limb distal to the position of the system 500 can be provided. Such compression can cause blood to flow in a vein to a greater extent, and in an opposite direction, than an artery. Accordingly, the control 540, using the data from the one or more ultrasound transducer(s) 580, can thereby distinguish the vein from the artery and identify the artery as the desired access vessel.

When the control system 540 identifies a desired access vessel and determines that the system 500 is suitably positioned relative to the patient such that the access needle 520 can be driven to enter the desired access vessel upon deployment, then the control system 540 can use the user interface 512 to provide instructions to the user to continue to hold the system 500 in the current position and to initiate deployment of the access needle 520. The user would continue to hold the system 500 against the patient at least until the access is obtained to the artery. Then, the access needle 520 will be automatically deployed to extend from the housing 510 via the needle deployment opening 530 and subcutaneously into the desired access vessel of the patient. Thereafter, the system can be held on the patient by being strapped around the patient and/or using adhesive to hold the housing 510 on the patient's skin.

The motive force for the deployment of the access needle 520 can be provided in various manners. In some embodiments, a spring can be used to force/fire the access needle 520 into the patient. For example, in some embodiments a spiral torsion spring can be used to drive the spool 560, which in turn can drive the access needle 520 and/or intravascular device (e.g., REBOA catheter 200 in this example). Such a spring can be wound a specific way to allow different lengths of catheter advancement, and spring stiffness can be used to regulate advancement speed. In particular embodiments, a motor can be used to force/fire the access needle 520 into the patient. For example, in some embodiments one or both of the guides 550a and 550b are friction drive wheels that can propel the access needle 520 and/or intravascular device (e.g., REBOA catheter 200 in this example) proximally and/or distally by being rotatably driven themselves by a motor or spring. In some cases the motor(s) that rotatably drive the guides 550a and 550b are electric. Alternatively, in some cases the motor(s) that rotatably drive the guides 550a and 550b are pneumatic (e.g., with a small turbine driven by compressed gas, such as from the on-board compressed gas canister(s) 570). In some embodiments, the spool 560 is rotatably driven (e.g., by a motor 562, FIG. 6, or a torsion spring, etc.) to distally advance and/or proximally retract the access needle 520 and/or intravascular device (e.g., using the column strength of the access needle 520 and/or intravascular device during advancement). It should be understood that any combination of such means for providing motive force to propel the access needle 520 and/or intravascular device (e.g., REBOA catheter 200) proximally and/or distally can be included in a system 500. For example, in some embodiments the guides 550*a* and 550*b* can be driven to advance the access needle 520 to achieve skin puncture, and thereafter the spool 560 can provide the motive force to advance/retract the access needle 520 and/or intravascular device.

In some embodiments, the system 500 can steer the access needle 520 while the access needle 520 is being advanced distally. For example, in some embodiments the access needle 520 can penetrate under the skin by about 0.5 cm and then the control system 540 (using the data from the one or more ultrasound transducer(s) 580) rescans, and then continues to advance the access needle 520 incrementally and to steer it along the way (while continuing to scan). In such a case, the scanning can also be used to visualize at least a tip portion of the access needle 520 so that the steering can be performed accurately.

In some embodiments, the access needle 520 includes a forward-looking ultrasound transducer 524 (e.g., in the manner of intravascular ultrasound, "IVUS") and/or a lateral-looking ultrasound transducer 526. The ultrasound transducer(s) 524 and/or 526, on-board the access needle 520, can be used in conjunction with the machine vision capabilities of the control system 540 to ascertain the location of the access needle 520 in relation to various anatomical landmarks such as vessel side branches (e.g., renal arteries, aortic arch, etc.) and other types of anatomical landmarks. Such information can be used by the system 500 to determine parameters pertaining to the automatic advancement of the access needle 520 and/or the intravascular device. The parameters can include, direction of advancement (steering), depth or distance of advancement, and the like.

With the access needle 520 now within the desired access vessel, the intravascular device (e.g., the REBOA endovascular stent graft device 200 in this example) can be advanced into the vessel. In some cases, the intravascular device is advanced over the access needle 520. In particular embodiments, the intravascular device is advanced through the access needle 520. Alternatively, in some embodiments the access needle 520 and the intravascular device are each advanced in the vessel (with the sharp tip of the access needle 520 being sheathed by the intravascular device, for example, for safety reasons).

As the intravascular device and/or access needle 520 is/are being advanced within the patient's vasculature, the ultrasound transducer(s) 524 and/or 526 (on-board the access needle 520) can be used in conjunction with the machine vision capabilities of the control system 540 to ascertain the location of the intravascular device and/or access needle 520 in relation to various anatomical landmarks such as vessel side branches (e.g., renal arteries, aortic arch, etc.) and other types of anatomical landmarks. In some embodiments, the intravascular device itself can alternatively or additionally include one or more ultrasound transducers that can be forward-looking, lateral-looking, or both forward-looking and lateral-looking. The system 500 can use the ascertained information to determine how far to advance the intravascular device and/or access needle 520 within the patient's vasculature.

In some embodiments, the system 500 can also include one or more load cells that would measure resistance when the intravascular device and/or access needle 520 is/are being advanced within the patient's vasculature. This will be helpful for determining whether the intravascular device and/or access needle 520 is/are being advanced within the patient's vasculature correctly, or is stuck against the wall of the aorta, or is misplaced in a smaller artery. If a certain amount of resistance is encountered by the load cell(s), the intravascular device and/or access needle 520 can be retrieved a certain distance back, rotated/adjusted, and then re-advanced again.

When the intravascular device is properly positioned within the patient's vasculature, the system 500 can then automatically or semi-automatically actuate/perform various functions to activate and control the intravascular device to treat the patient. For example, in the case of the REBOA endovascular stent graft device 200, the system 500 can perform the functional role of the control unit 280 (FIG. 1) as described above. Balloon inflation/deflation can occur automatically using the on-board compressed gas canister(s) 570 and solenoid valves integrated in the system 500.

In accordance with the description of the automated vascular access and endovascular device deployment/control system 500 provided herein, it should be understood that the system 500 can be used to treat a patient using an intravascular device in a significantly autonomous manner. For example, the vascular access, and other functions, is/are performed in an automated manner by the system 500. In some cases, the user can simply press the system 500 against a body part of the patient and then activate the system 500. Thereafter, the system 500 will perform the access, device deployment, and treatment automatically.

Additional Information

Utilizing established models for vascular dimensions based on age, torso length and other factors, the automated vascular access and endovascular device deployment/control system can potentially require no operator interaction after the initial deployment. Once attached to or simply pressed against the patient's body part, the system will automatically gain vascular access, advance the catheter contained within the device's housing, inflate and deflate the occlusion balloon (e.g., in the case of a REBOA catheter), deploy the aortic balloon shunt and monitor the patient's physiological state. Once the treatment is complete or advanced surgical care is available, the intravascular device is automatically retracted from the patient back into the device housing.

The automated vascular access and endovascular device deployment/control system described herein is an all-in-one operable unit that is attached to the patient's body by the care provider to initiate its use. The unit will have an interface, either on the device itself, attached to the device, or remotely transmitting information to the device via a network or other system, to activate deployment and allow input of the patient characteristics. Within the device there is a systems controller that processes the patient data through algorithms to determine the required catheter advancement length. Through a combination of internally programmed anatomical landmarks and ultrasound images, the system will guide the vascular access line out of the device and into the patient in the correct location.

After access is gained, the catheter is advanced the specific length into the aorta (or other artery). In the case of REBOA, the stent graft (or balloon shunt) is deployed to maintain blood flow to downstream tissues and organs and the occlusion balloon(s) are then deployed via inflation from a $CO_2$ canister or other gas/fluid source. Pressure monitors updated continuously determine which segments of the balloon(s) should continue inflating to occlude the aorta in the desired location. There are multiple potential methods of confirming correct catheter location and physiologic monitoring that include lower extremity body temperature monitoring, duplex ultrasound, X-ray, intravascular ultrasound, EKG monitoring, a local GPS system, or a certain amount of pressure in the occlusion balloon that distinguishes a small vessel from the aorta.

The present invention comprises a retrievable occluding stent graft (balloon shunt) that can overcome the problems associated with REBOA through an optimized design that will allow precise control of the blood flow to the downstream organs. The retrievable occluding stent-graft device can be delivered through the artery in the leg or arm and deployed at the site of aortic injury plus maintain the integrity and nourishment of the downstream organs.

In one embodiment the stent graft (shunt) portion of the device is made up of a retrievable self-expanding nitinol stent coated with a non-permeable synthetic graft fabric. Other types of stent grafts are also envisioned for use in this device.

In one embodiment the device contains multiple balloons. Balloons may surround the outside of the stent graft portion of the device. When inflated these balloons will block blood loss (occlude) from the aorta. The device may also contain balloons that are inside of the stent graft lumen to control the amount of blood that is shunted downstream of the injury. The balloons may be inflated using a variety of substances including but not limited to gases (including but not limited to $CO_2$, nitrogen helium etc.) and liquids (including but not limited to water, saline, phosphate buffered saline, etc.). In one embodiment the balloons are connect to a portable gas source such as $CO_2$ canisters. In another embodiment the balloons are connected to a saline or water reservoir.

The device of the present invention may be used with a variety of imaging systems including but not limited to ultrasound (such as duplex ultrasound and intravascular ultrasound), fluoroscopy, and X-ray. In one embodiment an ultrasound transducer is built into the catheter system to guide insertion of the device (vascular access) and to guide ultimate device placement within the body/vessel.

The device of the present invention can contain a variety of sensors. These sensors can be used to measure blood pressure and/or blood flow; temperature sensors, sensors to measure resistance of the advancing catheter, and the like. For example, such sensors will help the system determine which balloons of a REBOA catheter to inflate and how much to inflate the balloons to properly control bleeding. The sensors will feedback to the external control unit to provide real-time information to the caregiver.

In some embodiments, the device of the present invention will contain an external control unit. This unit may be connected to the device, sensors, monitors, infusion devices, and imaging equipment, for example. The control unit may contain a systems control unit that will house software and algorithms needed for the proper functioning of the device. Software can incorporate anatomical and physiological signals from the sensors and preprogramed data (such as aortic mechanical properties) into algorithms that will direct and control catheter function. In some embodiments, the software and algorithms will be used to determine vascular dimensions and position of key landmarks based on data from the sensors (such as inflated occlusion balloon pressure or ultrasound images of vessel dimensions) combined with patient data such as age, torso length, sex, and other factors to allow the device to function and deploy automatically. Other systems may be tied into the control unit and algorithms to help the device function and deploy properly such as EKG systems, GPS systems/sensors, temperature monitoring, imaging (including patient/subject specific imaging), and other necessary systems. The control unit will also contain a display allowing for the care giver to monitor the system.

The device of the present invention may be housed in a single unit that can be attached to a patient's leg or arm (or other area of insertion). Once attached to the patient, the system will be activated allowing the catheter containing the stent graft, balloons, sensors, gas or liquid reservoir (such as CO2 canisters), and any other incorporated systems (imaging) to leave the housing and be inserted into the patient. The housing may be made from a variety of materials including but not limited to plastic, resin, metal etc. In one embodiment, the catheter will be coiled up within the housing when not in use.

It is envisioned that this device will be portable and can be used in the field (on ambulances or other transport systems, or in the field). This system will be fully automated so that little skill or training is required by the operator to use the system. In one embodiment the device will be held against and/or attached to the patient at the desired site of insertion. The operator/care giver will then activate the device. The device will use built in imaging (e.g., ultrasound) to locate proper insertion point and then the device will deploy the needle and automatically insert the device into the patient. The device will then move within the vasculature automatically based on patient information put in by the user/care giver (age, sex, torso length, etc.) and/or on-board imaging sensors (e.g., IVUS), resistance sensors (loadcells), or other types of sensors. Sensors and imaging will also be used to identify the injury site and deploy the stent graft and balloons as needed. The device will then continuously monitor various readouts (blood pressure, etc.) and adjust balloon occlusion and blood flow through the stent graft shunt as needed until the patient reaches an operating room. The device can be used to treat a variety of internal bleeding injuries such as non-compressible hemorrhage.

In some embodiments, the device may also be used with GPS systems (i.e., a local positioning system of a specific body, not the global positioning system in the common sense) or EKG systems to help with device placement and deployment.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Accordingly, other embodiments are within the scope of the following claims.

What is claimed is:

1. An automated vascular access and endovascular device deployment and control system, the system comprising:
   a housing;
   a control system coupled to the housing;
   one or more ultrasound transducers coupled to the housing and configured for: (i) obtaining image data of subcutaneous structures while the housing is abutted against a skin surface of a patient and (ii) transmitting the image data to the control system;
   a vascular access needle movably coupled to the housing;
   an endovascular device movably coupled to the needle, the endovascular device comprising:
      a stent graft comprising an expandable tubular metallic frame and a covering material disposed on at least a portion of the metallic frame, wherein the stent graft defines a lumen that extends between a first end of the stent graft and a second end of the stent graft;
      a first balloon disposed around an outer periphery of the stent graft;
      a second balloon disposed around the outer periphery of the stent graft and spaced apart from the first balloon; and
      a third balloon disposed within the lumen at a location along the stent graft between the first balloon and the second balloon, the third balloon having a fully inflated configuration that fully occludes the lumen and a partially inflated configuration that partially occludes the lumen for modulating blood flow through the stent graft; and
   one or more drive systems configured to drive the needle and the endovascular device to extend from the housing and to retract into the housing.

2. The system of claim 1, wherein the system is sized to be used in a hand-held manner.

3. The system of claim 1, wherein the needle is movable, relative to the housing, between a retracted position in which the needle is within the housing and an extended position in which the needle is outside of the housing or extending away from the housing.

4. The system of claim 1, wherein the one or more drive systems comprises a motor coupled to a pair of rotary guides that are frictionally engaged with an outer surface of the needle so that the rotary guides will move the needle when the rotary guides are rotated by the motor.

5. The system of claim 1, wherein the one or more drive systems comprises a spring that provides motive force to move the needle relative to the housing.

6. The system of claim 1, further comprising a spool and wherein at least a portion of the endovascular device is wound around the spool.

7. The system of claim 6, wherein the spool is rotatably driven by the one or more drive systems.

8. The system of claim 1, further comprising a compressed gas canister in fluid communication with an inflatable member of the endovascular device.

9. The system of claim 8, further comprising a solenoid valve in communication with the control system and arranged to control a flow of gas from the compressed gas canister to the inflatable member.

10. The system of claim 1, wherein the control system is configured to control inflation and deflation of each of the first, second, and third balloons individually.

11. The system of claim 1, further comprising one or more additional ultrasound transducers coupled to the needle.

12. A system comprising:
   a housing containing a control system;
   an ultrasound transducer coupled to the housing;
   a vascular access needle movably coupled to the housing;
   an endovascular device movably coupled to the needle, the endovascular device comprising:
      a stent graft comprising an expandable tubular metallic frame and a covering material disposed on at least a portion of the metallic frame, wherein the stent graft defines a lumen that extends between a first end of the stent graft and a second end of the stent graft;
      a first balloon disposed around an outer periphery of the stent graft;
      a second balloon disposed around the outer periphery of the stent graft and spaced apart from the first balloon; and
      a third balloon disposed within the lumen at a location along the stent graft between the first balloon and the second balloon, the third balloon having a fully inflated configuration that fully occludes the lumen and a partially inflated configuration that partially occludes the lumen for modulating blood flow through the stent graft; and
   one or more drive systems coupled to the housing and configured to drive the needle and the endovascular device to extend from the housing and to retract into the housing.

13. The system of claim 12, wherein the ultrasound transducer is configured for: (i) obtaining image data of subcutaneous structures while the housing is abutted against a skin surface of a patient and (ii) transmitting the image data to the control system.

14. The system of claim 12, wherein the system is sized to be used in a hand-held manner.

15. The system of claim 12, further comprising an additional ultrasound transducer coupled to the needle.

16. The system of claim 12, wherein the control system is configured to control inflation and deflation of each of the first, second, and third balloons individually.

17. The system of claim 12, further comprising a spool and wherein at least a portion of the endovascular device is wound around the spool.

18. The system of claim 12, wherein the one or more drive systems comprises a spring that provides motive force to move the needle relative to the housing.

* * * * *

UNITED STATES PATENT AND TRADEMARK OFFICE
CERTIFICATE OF CORRECTION

| | | |
|---|---|---|
| PATENT NO. | : 12,138,186 B2 | Page 1 of 1 |
| APPLICATION NO. | : 17/258100 | |
| DATED | : November 12, 2024 | |
| INVENTOR(S) | : Jason N. MacTaggart, Alexey Kamenskiy and Blake Marmie | |

It is certified that error appears in the above-identified patent and that said Letters Patent is hereby corrected as shown below:

In the Specification

In Column 1, Line 8, delete "8371" and insert -- § 371 --.

Signed and Sealed this
Thirty-first Day of December, 2024

Derrick Brent
*Acting Director of the United States Patent and Trademark Office*